(12) United States Patent
Kuslich (10) Patent No.: US 9,526,621 B2
(45) Date of Patent: Dec. 27, 2016

(54) EXPANDABLE POROUS MESH BAG DEVICE AND METHODS OF USE FOR REDUCTION, FILLING, FIXATION AND SUPPORTING OF BONE

(71) Applicant: Spineology, Inc., St. Paul, MN (US)

(72) Inventor: Stephen D. Kuslich, Stillwater, MN (US)

(73) Assignee: Spineology Inc., St. Paul, MN (US)

( * ) Notice: Subject to any disclaimer, the term of this patent is extended or adjusted under 35 U.S.C. 154(b) by 0 days.

(21) Appl. No.: 14/016,866

(22) Filed: Sep. 3, 2013

(65) Prior Publication Data

US 2014/0067066 A1 Mar. 6, 2014

Related U.S. Application Data

(60) Continuation of application No. 11/282,910, filed on Nov. 18, 2005, now abandoned, which is a division of
(Continued)

(51) Int. Cl.
*A61F 2/44* (2006.01)
*A61B 17/68* (2006.01)
(Continued)

(52) U.S. Cl.
CPC ............ *A61F 2/441* (2013.01); *A61B 17/68* (2013.01); *A61B 17/7098* (2013.01);
(Continued)

(58) Field of Classification Search
CPC . A61B 17/1671; A61B 17/1757; A61B 17/88; A61B 17/8805; A61B 17/885; A61B 17/7097; A61B 17/7098; A61B 17/8852; A61B 17/8855; A61B 17/8858; A61B 17/3472; A61B 2017/56; A61B 2017/564; A61F 2/441; A61F 2/4601; A61F 2002/2846; A61F 2002/4495; A61F 2002/4601; A61F 2002/4602; A61F 2002/2817; A61F 2002/30011
(Continued)

(56) References Cited

U.S. PATENT DOCUMENTS 4,969,888 A 11/1990 Scholten et al.
5,015,255 A * 5/1991 Kuslich .................. 128/898
(Continued)

FOREIGN PATENT DOCUMENTS

EP 0836435 B1 4/1998
EP 0886506 B1 12/1998
(Continued)

OTHER PUBLICATIONS

Request for reexamination of U.S. Pat. No. 7,226,481 (Reexam Control No. 95/002,179), filed Sep. 11, 2011, 256 pages.
(Continued)

*Primary Examiner* — Lynnsy Summitt
(74) *Attorney, Agent, or Firm* — Skaar Ulbrich Macari, P.A.

(57) ABSTRACT

The invention provides a method of correcting numerous bone abnormalities including bone tumors and cysts, avascular necrosis of the femoral head, tibial plateau fractures and compression fractures of the spine. The abnormality may be corrected by first accessing and boring into the damaged tissue or bone and reaming out the damaged and/or diseased area using any of the presently accepted procedures or the damaged area may be prepared by expanding a bag within the damaged bone to compact cancellous bone. After removal and/or compaction of the damaged tissue the bone is stabilized.

14 Claims, 13 Drawing Sheets

Related U.S. Application Data application No. 10/440,036, filed on May 16, 2003, now Pat. No. 7,226,481, which is a continuation of application No. 09/909,667, filed on Jul. 20, 2001, now abandoned.

(60) Provisional application No. 60/219,853, filed on Jul. 21, 2000.

(51) Int. Cl.

| | | |
|---|---|---|
| *A61B 17/70* | (2006.01) | |
| *A61B 17/74* | (2006.01) | |
| *A61B 17/00* | (2006.01) | |
| *A61B 17/16* | (2006.01) | |
| *A61B 17/32* | (2006.01) | |
| *A61B 17/34* | (2006.01) | |
| *A61B 17/88* | (2006.01) | |
| *A61F 2/00* | (2006.01) | |
| *A61F 2/34* | (2006.01) | |
| *A61F 2/46* | (2006.01) | |
| *A61F 2/28* | (2006.01) | |
| *A61F 2/30* | (2006.01) | |

(52) U.S. Cl.
CPC ........ *A61B 17/742* (2013.01); *A61B 17/8855* (2013.01); *A61F 2/4611* (2013.01); *A61B 17/00234* (2013.01); *A61B 17/1617* (2013.01); *A61B 17/1668* (2013.01); *A61B 17/1671* (2013.01); *A61B 17/1675* (2013.01); *A61B 17/32002* (2013.01); *A61B 17/3472* (2013.01); *A61B 17/8805* (2013.01); *A61B 2017/00004* (2013.01); *A61B 2017/00261* (2013.01); *A61B 2017/00557* (2013.01); *A61F 2/0095* (2013.01); *A61F 2/34* (2013.01); *A61F 2/44* (2013.01); *A61F 2/461* (2013.01); *A61F 2/4601* (2013.01); *A61F 2/4607* (2013.01); *A61F 2002/2817* (2013.01); *A61F 2002/2828* (2013.01); *A61F 2002/2832* (2013.01); *A61F 2002/2835* (2013.01); *A61F 2002/2892* (2013.01); *A61F 2002/3025* (2013.01); *A61F 2002/30034* (2013.01); *A61F 2002/30069* (2013.01); *A61F 2002/30271* (2013.01); *A61F 2002/30448* (2013.01); *A61F 2002/30451* (2013.01); *A61F 2002/30581* (2013.01); *A61F 2002/30718* (2013.01); *A61F 2002/448* (2013.01); *A61F 2002/4602* (2013.01); *A61F 2002/4635* (2013.01); *A61F 2002/4636* (2013.01); *A61F 2220/005* (2013.01); *A61F 2220/0058* (2013.01); *A61F 2230/0071* (2013.01); *A61F 2230/0082* (2013.01); *A61F 2250/0031* (2013.01); *A61F 2310/00293* (2013.01); *A61F 2310/00353* (2013.01)

(58) Field of Classification Search
USPC ............... 606/94, 105; 623/17.11, 17.12
See application file for complete search history.

(56) References Cited

U.S. PATENT DOCUMENTS

| | | | |
|---|---|---|---|
| 5,549,679 A * | 8/1996 | Kuslich | ............... 623/17.12 |
| 5,571,189 A | 11/1996 | Kuslich | |
| 5,997,582 A | 12/1999 | Weiss | |
| 6,607,544 B1 | 8/2003 | Boucher et al. | |
| 6,726,691 B2 | 4/2004 | Osorio et al. | |
| 6,740,093 B2 * | 5/2004 | Hochschuler et al. | ......... 606/94 |

FOREIGN PATENT DOCUMENTS

| | | |
|---|---|---|
| EP | 1083836 B1 | 3/2001 |
| WO | 9902214 A1 | 1/1999 |

OTHER PUBLICATIONS

Order granting inter partes reexamination of U.S. Pat. No. 7,226,481 (Reexam Control No. 95/002,179), mailed Dec. 7, 2012, 18 pages.
Non-final office action in Reexam No. 95/002,179, mailed Dec. 7, 2012, 11 pages.
Patent Owner's Response to Non-final office action in Reexam No. 95/002,179, filed Feb. 7, 2013, 34 pages.
First Declaration of James H. Maxwell, M.D in inter-partes reexamination 95/002,179, Feb. 7, 2013, 9 pages.
Declaration of Scott G. Ulbrich in inter-partes reexamination 95/002,179, Feb. 7, 2013, 39 pages.
Comments by Third Party Requester in Reexam No. 95/002,179, filed Mar. 11, 2013, 44 pages.
Declaration of F. Calame Sammons, M.D. in inter-partes reexamination 95/002,179, Mar. 11, 2013, 19 pages.
Action Closing Prosecution (Non-final) in Reexam No. 95/002,179, mailed Jul. 30, 2013, 60 pages.
Patent Owner's Response to Action Closing Prosecution in Reexam No. 95/002,179, filed Sep. 30, 2013, 34 pages.
Second Declaration of James H. Maxwell, M.D, filed in inter-partes reexamination 95/002,179 on Sep. 30, 2013, 10 pages.
Declaration of Steven J. Wolfe (dated Jul. 9, 2004), filed in inter-partes reexamination 95/002,179 on Sep. 30, 2013, 14 pages.
Declaration of Stephen D. Kuslich, M.D (dated Jul. 12, 2004), filed in inter-partes reexamination 95/002,179 on Sep. 30, 2013, 45 pages.
Declaration of Steven J. Wolfe (dated Sep. 30, 2013), filed in inter-partes reexamination 95/002,179 on Sep. 30, 2013, 10 pages.
Comments by Third Party Requester in Reexam No. 95/002,179, filed Oct. 30, 2013, 47 pages.
Second Declaration of F. Calame Sammons, M.D. in inter-partes reexamination 95/002,179, Mar. 11, 2013, 9 pages.
Right of Appeal Notice in Reexam No. 95/002,179, mailed Jan. 23, 2014, 59 pages.
Patent Owner's Appeal Brief in Reexam No. 95/002,179, filed Apr. 24, 2014, 67 pages.
Third Party Requester's Appeal Respondent's Brief in Reexam No. 95/002,179, filed May 27, 2-14, 44 pages.
Osorio, Rey, et al., U.S. Appl. No. 60/194,685, filed Apr. 5, 2000, entitled "Methods and Devices for Treating Bone," 60 pages.

* cited by examiner

EXPANDABLE POROUS MESH BAG DEVICE AND METHODS OF USE FOR REDUCTION, FILLING, FIXATION AND SUPPORTING OF BONE

CROSS-REFERENCE TO RELATED APPLICATIONS

This application is a continuation of U.S. patent application No. 11/282,910, filed Nov. 18, 2005, which is a divisional application of U.S. patent application No. 10/440,036, filed May 16, 2003, now U.S. Pat. No. 7,226,481, which claims priority to U.S. patent application No. 09/909,667, filed Jul. 20, 2001, which claims priority to U.S. Provisional Application No. 60/219,853 filed Jul. 21, 2000, the entirety of each of the foregoing applications are hereby incorporated herein by reference.

BACKGROUND OF THE INVENTION

This invention relates to methods and devices for correcting bone abnormalities and involves the use of a surgical mesh bag which is inserted into a prepared cavity in bone. The bag is inflated using bone replacement material to expand and fill the cavity.

U.S. Pat. Nos. 5,549,679 and 5,571,189 to Kuslich, describe a device and method for stabilizing the spinal segment with an expandable, porous fabric implant for insertion into the interior of a reamed out disc which is packed with material to facilitate bony fusion. In the present invention, a similar bag is used to correct bone abnormalities including, but not limited to, bone tumors and cysts, tibial plateau fractures, avascular necrosis of the femoral head and compression fractures of the spine.

U.S. Pat. Nos. 5,108,404 and 4,969,888 to Scholten et al., describe a system for fixing osteoporotic bone using an inflatable balloon which compacts the bone to form a cavity into which bone cement is injected after the balloon is withdrawn. The invention requires the use of fluoroscopy to monitor the injection and to help guard against cement leakage through fissures in bone. Unfortunately, such leakage is known to occur in spite of these precautions. Since such leakage may cause serious injury, including paralysis, an improved device and method is needed.

U.S. Pat. No. 5,972,015 to Scribner et al., describes a system of deploying a catheter tube into the interior of a vertebra and expanding a specially configured nonporous balloon therewithin to compact cancellous bone to form a cavity. The Scribner patent approach utilizes a non-porous balloon which is inflated within the bone to cause compression. The cavity thus formed, may then be filled with bone cement. Unfortunately, the bag used by Scribner may be ruptured during expansion to compact cancellous bone due to sharp projections found within the cavity to be expanded. Filling the cavity eventually formed could allow leakage of bone cement out of the bone against vessels or nerves which may cause undesirable complications.

The present invention involves an improvement of all of the previous techniques and avoids complications that could occur with the system of U.S. Pat. No. 5,972,015.

All U.S. patents, applications and all other published documents mentioned anywhere in this application are incorporated herein by reference in their entirety.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The invention provides a method of correcting numerous bone abnormalities including bone tumors and cysts, avascular necrosis of the femoral head, tibial plateau fractures and compression fractures of the spine. The abnormality may be corrected by first accessing and boring into the damaged tissue or bone and reaming out the damaged and/or diseased area using any of the presently accepted procedures, or the damaged area may be prepared by expanding a bag within the damaged bone to compact cancellous bone. After removal and/or compaction of the damaged tissue the bone must be stabilized.

In cases in which the bone is to be compacted, the methods and devices of this invention employ a catheter tube attached to an inflatable porous fabric bag as described in U.S. Pat. Nos. 5,549,679 and 5,571,189 to Kuslich, the disclosures of which are incorporated herein by reference. Those bags may be inflated with less fear of puncture and leakage of the inflation medium than thin walled rubber balloons. They may also be used over a Scribner balloon to protect the balloon from breakage and eventually seepage.

The devices of U.S. Pat. Nos. 5,549,679 and 5,571,189 to Kuslich, additionally provide the surgeon with the advantage of safely skipping the first balloon inflation steps of Scribner and Scholten, by expanding the bag through introduction of fill material, such as a bone repair medium thereby correcting the bony defect and deformity and stabilizing it in one step of the procedure.

As indicated above, the damaged bone may be removed by any conventional reamer. Examples of reamers are described in U.S. Pat. No. 5,015,255; U.S. patent application No. 09/782,176, to Kuslich et al., entitled "Expandable Reamer" and filed Feb. 13, 2001; and U.S. patent application No. 09/827,202 to Peterson et al., entitled "Circumferential Resecting Reamer Tool," filed Apr. 5, 2001. Other examples of reamers are known and may be used. After the damaged bone or tissue has been removed, bone repair medium may then be inserted into the cavity thus formed, via a catheter and expandable fabric bag as described in U.S. Pat. Nos. 5,549,679 and 5,571,189.

Alternatively, either a smaller than desired cavity may be formed into the bone to be enlarged by compaction or the cavity may be formed only by compaction through introduction of fill material into the bag. In either case, the bag may be positioned over the inflation balloon which is then inflated within the bone site to provide the degree of compaction required. The bag may then be filled with fill material, such as bone repair medium while the balloon remains in place within the bag. Alternatively, the balloon may be removed from the bag prior to filing the bag.

BRIEF DESCRIPTION OF THE DRAWINGS

A detailed description of the invention is hereafter described with specific reference being made to the drawings in which.

DETAILED DESCRIPTION OF THE PREFERRED EMBODIMENTS

In the following detailed description, similar reference numerals are used to depict like elements in the various figures.

Figure 1:
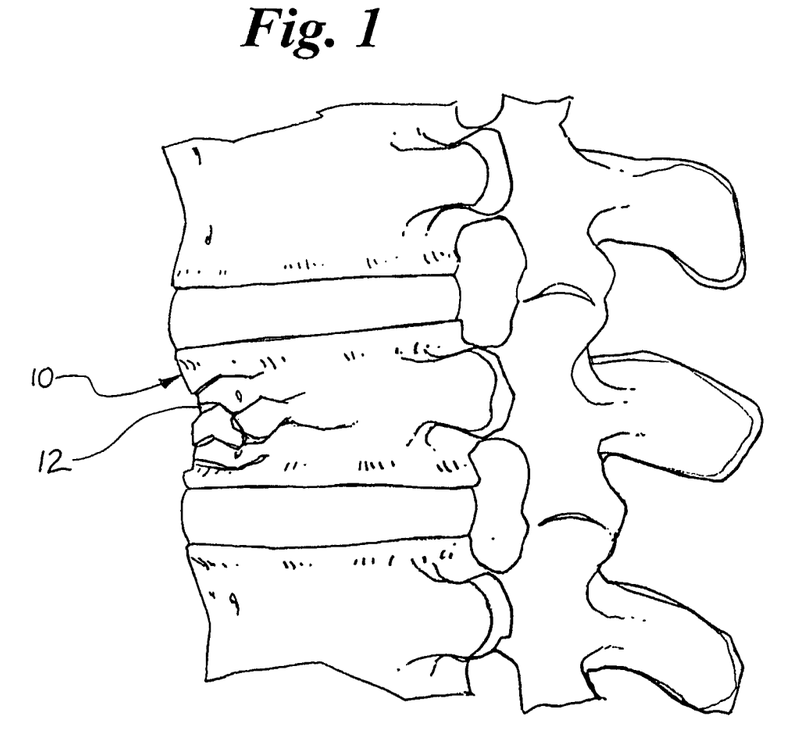
FIG. 1 is a side elevational view of a vertebra that is fractured and in need of repair.
Figure 2:
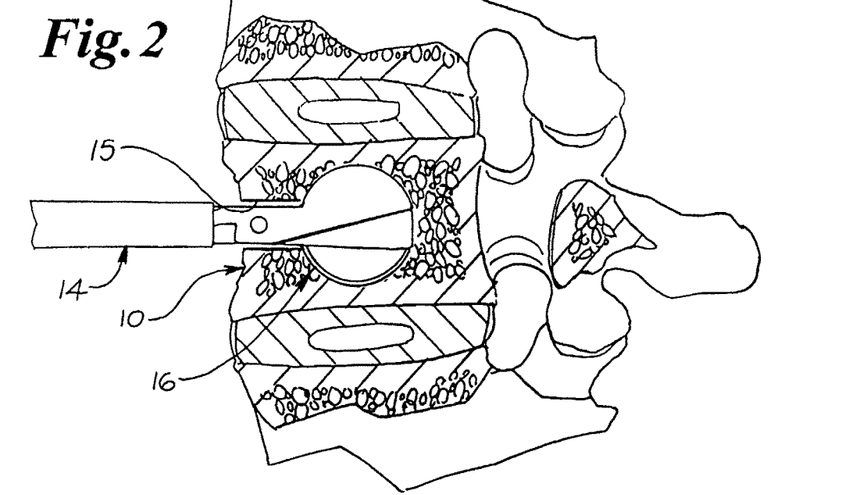
FIG. 2 is a side view of the vertebra of FIG. 1 being reamed out with a reaming tool from the anterior approach.
Figure 3:
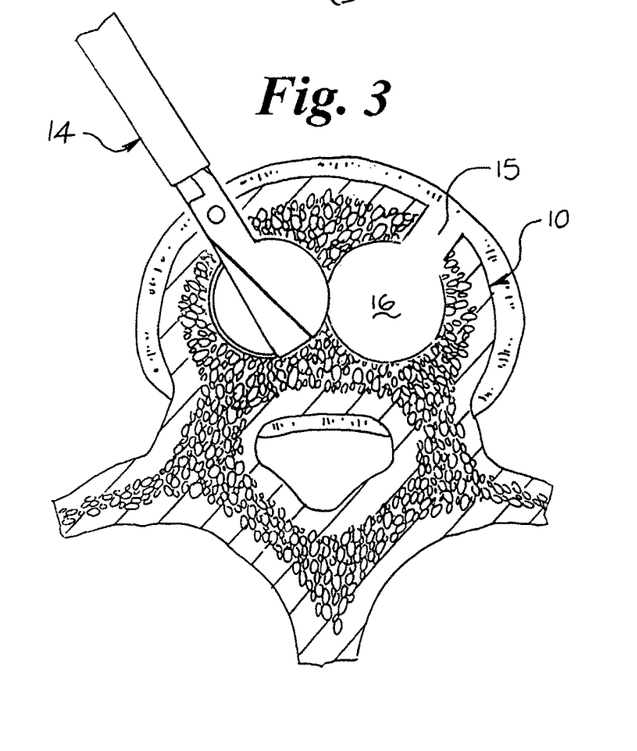
FIG. 3 is a top view of the vertebra of FIG. 1 showing the reamer forming a pair of cavities within the vertebra from the anterior approach.

FIG. 1 shows a typical vertebra 10 having compression fractures 12 that is in need of repair. As indicated above the damaged portion of the vertebra 10 may be reamed out, compacted, or otherwise repaired. For example, FIG. 2 shows a reamer 14 entering the vertebra 10 anteriorly to make an opening 15 and cavity 16. Alternatively, multiple cavities 16 may be formed such as is shown in FIG. 3.

Figure 4:
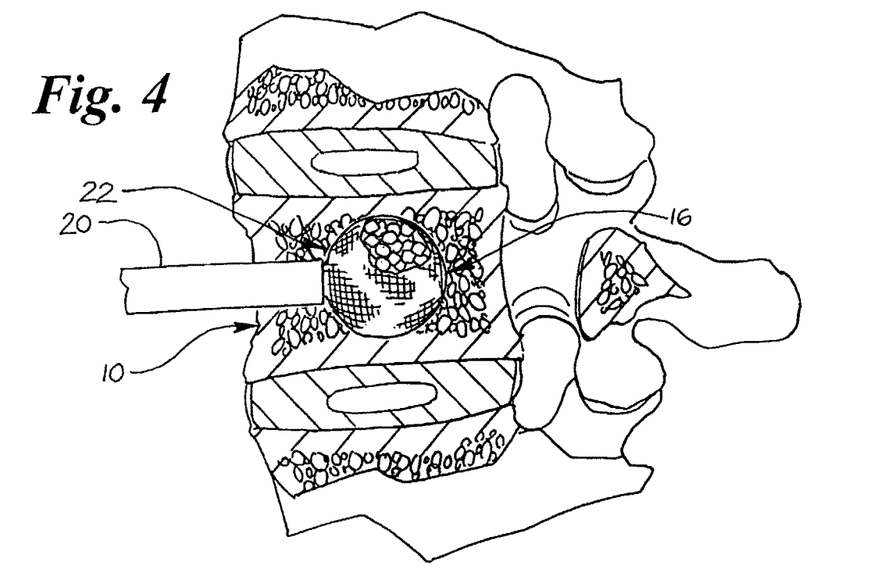
FIG. 4 is a side elevational view of the vertebra of FIG. 2 showing placement of an expandable fabric bag of the invention.

As previously mentioned, the damaged portion of the vertebra 10 may be compacted in addition to or instead of being reamed out. In FIG. 4, a delivery tube or catheter 20 is seen in the process of delivering an expandable fabric bag 22 into the vertebra 10 or into a cavity 16 present therein. As indicated, the cavity 16 may have been created through reaming, compaction by the bag 22 or other device, or by other means. Once the bag 22 is positioned within the vertebra 10, the bag 22 may be inflated or expanded to the limits of the cavity 16 thus formed through insertion or injection of fill material 19 into the interior 21 of the bag 22.

Figure 5:
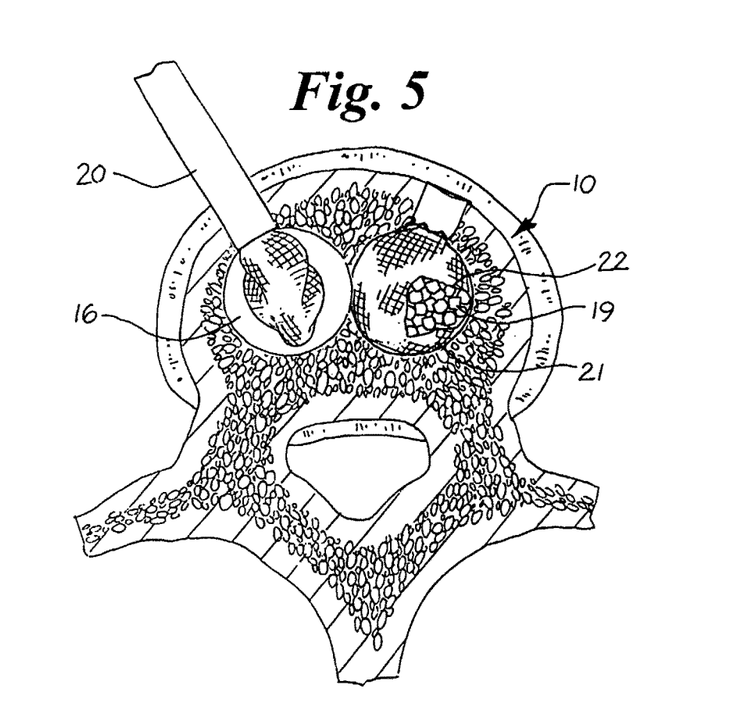
FIG. 5 is a top elevational view of the vertebra of FIG. 3 showing a second of two expandable fabric bags of the invention being positioned.
Figure 6:
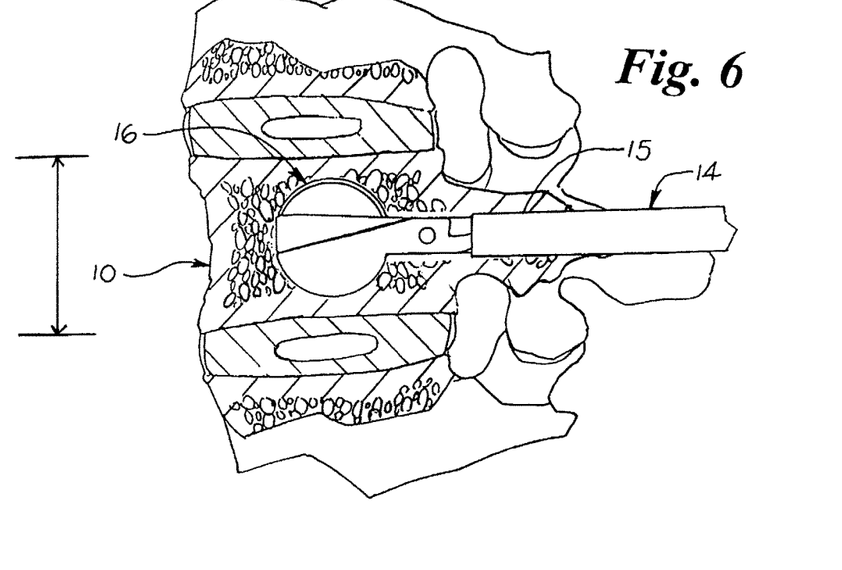
FIG. 6 is a side view of a vertebra being reamed from a posterior approach.
Figure 7:
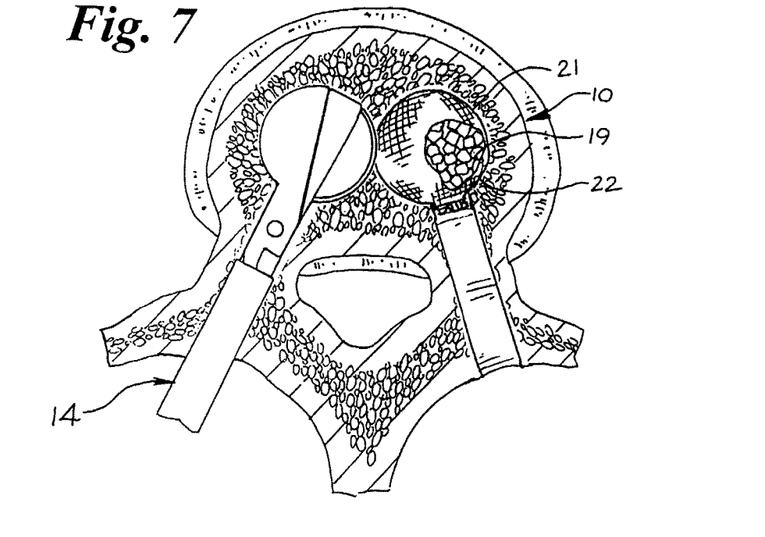
FIG. 7 is a top view of the vertebra of FIG. 6 with a bag in place and a second cavity being reamed.
Figure 8:
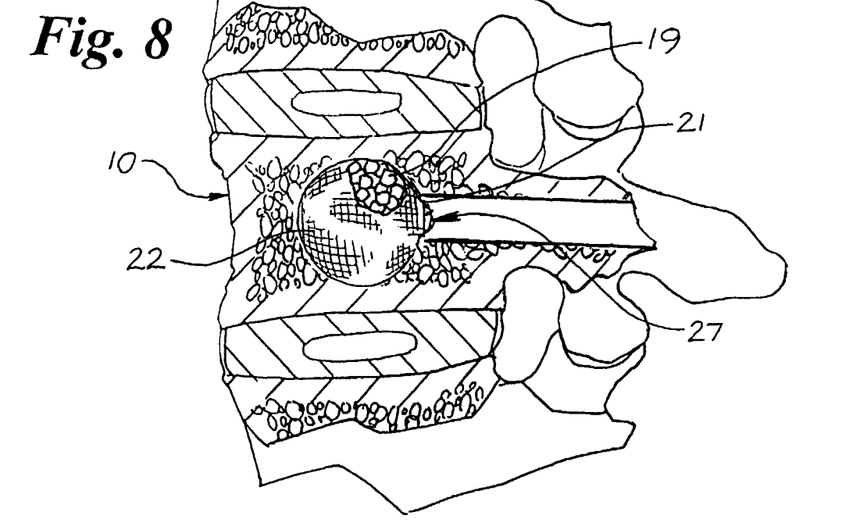
FIG. 8 is a side elevational view of the vertebra of FIG. 6 with an expandable fabric bag of the invention in place.

FIG. 5 shows a single filled expandable fabric bag 22 in place with a second expandable bag which is being inserted and expanded within the cavity 16.

FIGS. 6-9 illustrate a procedure in which the opening 15 and cavity 16 are created posteriorly. Regardless of the direction through which the vertebra 10 is operated on, in all forms, the cavity 16 which is formed is then filled with acceptable bone replacement material.

Bone replacement material 19 may be one or more of the following, or any other biocompatible material judged to have the desired physiologic response:

A) Demineralized bone material, morselized bone graft, cortical, cancellous, or cortico-cancellous, including autograft, allograft, or xenograft;

B) Any bone graft substitute or combination of bone graft substitutes, or combinations of bone graft and bone graft substitutes, or bone inducing substances, including but not limited to: Tricalcium phosphates, Tricalcium sulfates, Tricalcium carbonates, hydroxyapatite, bone morphogenic protein, calcified and/or decalcified bone derivative; and C) Bone cements, such as ceramic and polymethylmethacrylate bone cements. The bone replacement material is inserted into the bag 22 via a needle, catheter 20 or other type of fill tool. The bone replacement material expands the bag to the limits of the cavity 16.

The inventive bag 22 may be a small fabric bag, from about one to about four cm in diameter, being roughly spherical in shape, although other elliptical shapes and other geometric shapes may be used. The bag is pliable and malleable before its interior space 21 is filled with the contents to be described. The material of the bag 22 may be configured to take on the shape of the cavity in which the bag is placed. While in this initial condition, the bag may be passed, uninflated, through a relatively small tube or portal, perhaps about three mm to about one cm in diameter.

Figure 9:
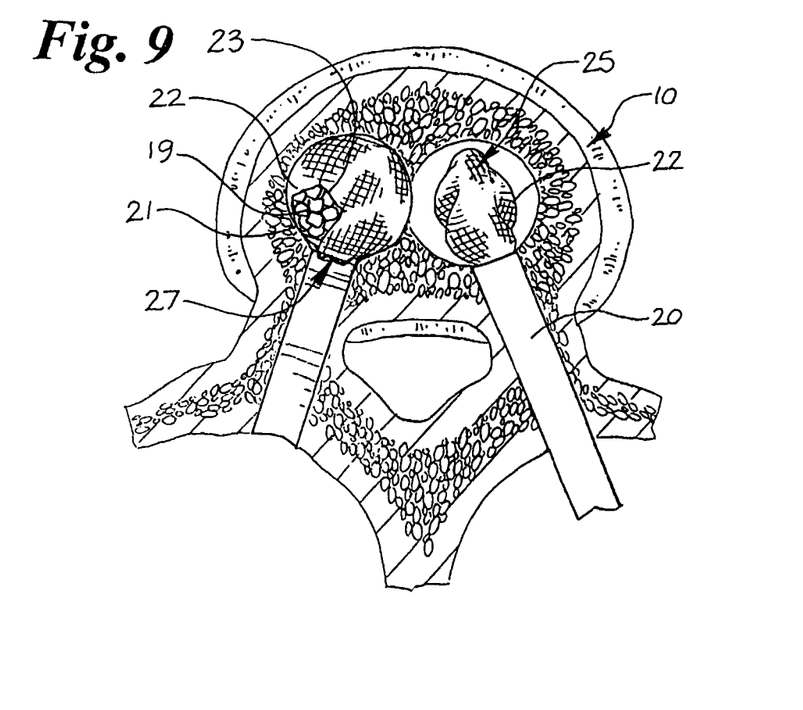
FIG. 9 is a top view of the vertebra of FIG. 7 with one bag inflated and the second bag being deployed.
Figure 10:
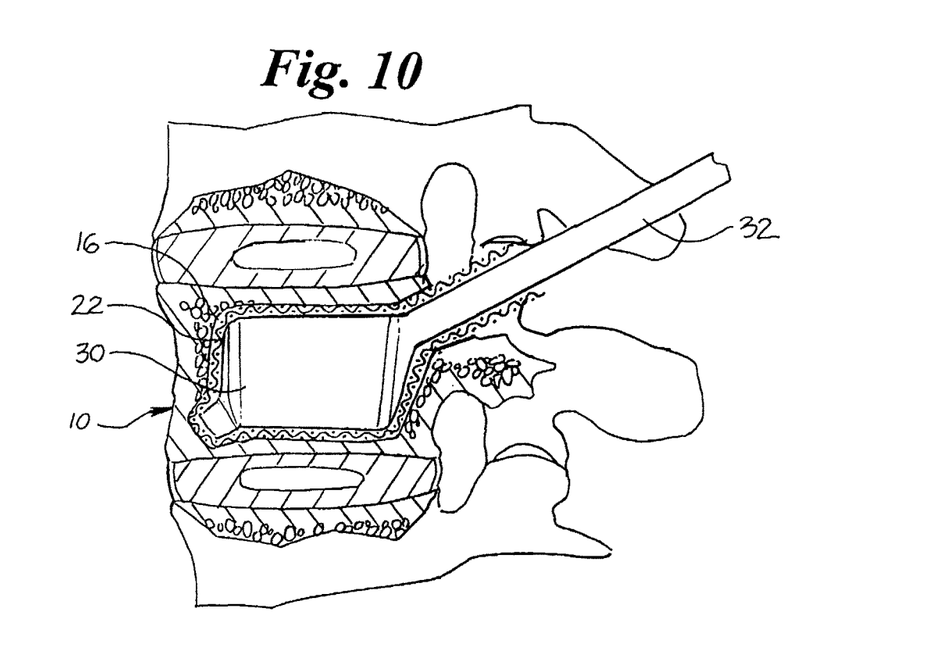
FIG. 10 is a side elevational view showing the vertebra cavity being expanded with an expandable fabric bag about an inflation device in cross-section.

The bag 22, such as may best be seen in FIG. 9, is constructed in a special and novel way. The bag 22 may be constructed of a fabric 23. Fabric 23 may be woven, knitted, braided or form-molded to a density that will allow ingress and egress of fluids and solutions and will allow the ingrowth and through-growth of blood vessels and fibrous tissue and bony trabeculae, but the fabric porosity is tight enough to retain small particles of enclosed material, such as ground up bone graft, or bone graft substitute such as hydroxyapatite or other osteoconductive biocompatible materials known to promote bone formation. The fabric 23 defines a plurality of pores 25. Generally, the pores 25 of the fabric 23 will have a diameter of about 0.25 mm or less to about 5.0 mm. The size is selected to allow tissue ingrowth while containing the material packed into the bag. If bone cement or other material is used which will not experience bone ingrowth, the pores 25 may be much tighter to prevent egress of the media from within the bag 22 out into the cavity 16. This prevents leakage that could impinge upon nerves, blood vessels or the like if allowed to exit the bone.

One or more of the pores 25 may be used as a fill opening 27, wherein the fabric 23 may be manipulated to enlarge a pore to a diameter potentially greater than 5 mm but no more than about 1 cm. Preferably, the fill opening 27 is less than about 5 mm in diameter. Such a pore/fill opening 27 is sufficiently large to allow a catheter, needle, fill tube or other device for inserting or injecting fill material to pass through the fabric 23 and into the interior 21 of the bag 22 without damaging the integrity of the bag 22.

When the bag 22 is fully filled with fill material, the bag will form a self-retaining shape which substantially fills the cavity 16. Once sufficiently full, the fill tool used to place fill material into the bag interior 21 is removed from the opening 27. Where the opening 27 is not a pore 25 but rather a separate and distinct opening in the bag 22, the opening 27 may have a set diameter which requires sealing such as by tying, fastening, welding, gluing or other means of closing the opening 27 after the bag has been filled. Where the opening 27 is a pore 25, upon removal of the catheter or fill tool from the opening 27 the fabric 23 will contract to reduce the diameter of the opening 27 to be substantially similar to that of the other pores 25.

The size and density of the pores determine the ease or difficulty with which materials may pass through the mesh. For instance, very small pores (<0.5 mm) would prohibit passage of all but the smallest particles and liquids. The pore size and density could be controlled in the manufacturing process, such that the final product would be matched to the needs of the surgeon. For example, if methylmethacrylate bone cement were to be used, the pore size would need to be very small, such as about less than 0.5 mm to about 1.0 mm, whereas, when bone graft or biocompatible ceramic granules are used, pore sizes ranging from about 1.0 mm to about 5.0 mm or more may be allowed. The fact that the fabric 23 is properly porous would allow it to restrict potentially dangerous flow of the fill material outside the confines of the bag.

The fabric is light, biocompatible, flexible and easily handled, and has very good tensile strength, and thus is unlikely to rip or tear during insertion and inflation. When the device is inflated, the device expands to fill a previously excavated cavity 16.

The use of the term "fabric" herein is meant to include the usual definition of that term and to include any material that functions like a fabric, that is, the "fabric" of the invention must have a plurality of pores 25 through which material and fluid flow is allowed under the terms as described, and the "fabric" must be flexible enough to allow it to be collapsed and inserted into an opening smaller than the inflated bag size.

The bag 22 need not be woven and may be molded or otherwise formed as is well known in the art. The preferred material may provide the ability to tailor bioabsorbance rates. Any suture-type material used medically may be used to form the bag 22. The bag may be formed of plastic or even metal. In at least one embodiment, bag 22 is formed using a combination of resorbable and/or nonresorbable thread. Bag 22 may include a fill opening 27 which may be a bushing that could be a bioabsorbable and/or nonbioabsorbable plastic, ceramic or metal. The opening 27 may also be hydroxyapatite, or it could be plastic or metal. The opening 27 may also be characterized as a pore 25, wherein a pore 25 of the fabric 23 has been expanded to allow a catheter 20 or other fill device to pass into the interior 21 of the bag 22. The bag 22 could be formed from a solid material to which perforations are added. The bag 22 may be partially or totally absorbable, metal, plastic, woven, solid, film or an extruded balloon.

In embodiments of the present invention a damaged tissue of a body, such as a vertebra 10 may be treated in accordance with the following procedures such as are depicted in FIGS. 1-9:

Initially, the vertebra 10 needing repair is surgically exposed by forming at least one cavity 16. The cavity or cavities 16 may be formed by several different means such as by reaming. Reaming may be accomplished by several means such as including the use of a reamer 14 such as, for example, the Kuslich Expandable Reamer, U.S. Pat. No. 5,015,255, the entire content of which is incorporated herein by reference. Next, the unexpanded mesh bag or Expandable Fabric Bag Device (EFBD) 22 is inserted into the cavity or cavities via catheter 20 or other means. At some point, the fill material 19 is prepared for insertion or injection into the EFBD 22. Following preparation of the fill material 19, the material is injected or otherwise inserted into the bag 22 using sufficient pressure to fill the bag 22 to its expanded state, thus producing rigidity and tension within the cavity or cavities 16 to reach the degree of correction required by virtue of the compression fractures. Finally, the fill opening 27 is closed to prevent egress of inflation material 19.

FIGS. 10-15 show a form of the invention in which a balloon 30 and catheter tube 32 is employed. The balloon 30 is surrounded by an expandable fabric bag 22 to protect the balloon 30 from being punctured during the inflation steps and to remain in place to prevent undesired egress of material injected into the cavity formed in the bone. Balloon 30 may be any medical-grade elastomeric balloon. The balloon 30 may be constructed from latex, urethanes, thermoplasic elastomers or other substances suitable for use as an expandable member. Examples of suitable balloons include, but are not limited to: balloons utilized with the FOGARTY®. occlusion catheter manufactured by Baxter Healthcare Corporation of Santa Ana, Calif.; balloons of the type described in U.S. Pat. No. 5,972,015 to Scribner et al., and others. The methods involve placement of the expandable fabric bag 22 of the invention about the balloon 30 of the Scribner et al. device. The expandable bag 22 is left in place before the cavity 16 is filled with bone substitute or bone cement. The expandable fabric bag 22 prevents breakage of the balloon 30 and greatly limits the ability of fill material from leaking out of the cavity through bone fissures where it could cause damage.

Figure 11:
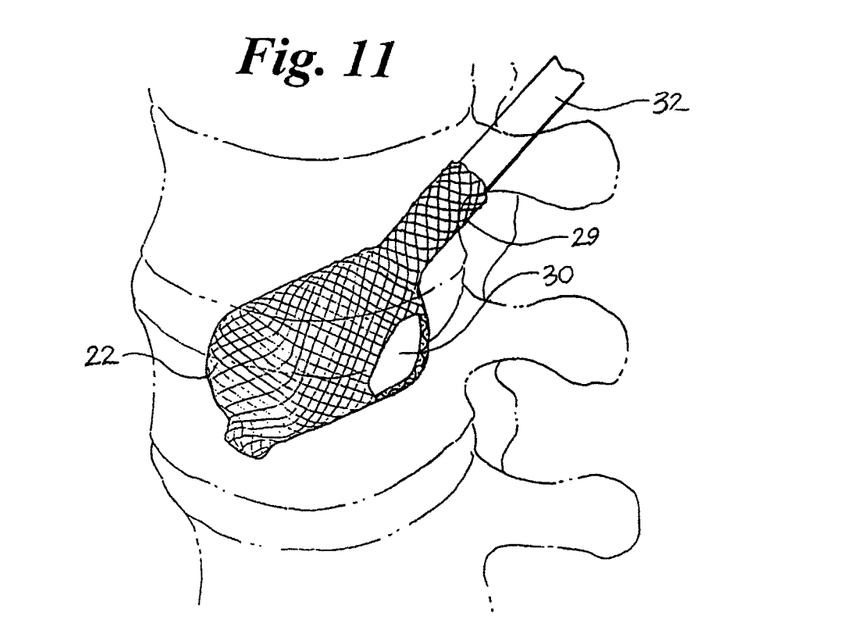
FIG. 11 shows the bag system of FIG. 10 with the vertebra in phantom to show the bag system.
Figure 12:
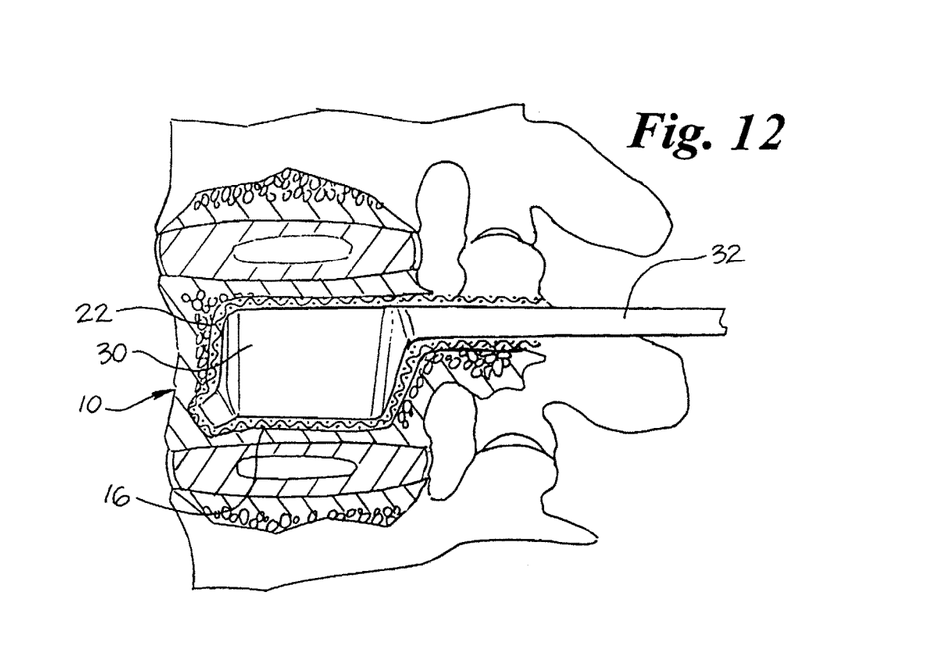
FIG. 12 is a view similar to FIG. 10 showing a different approach to the interior of the vertebra.
Figure 13:
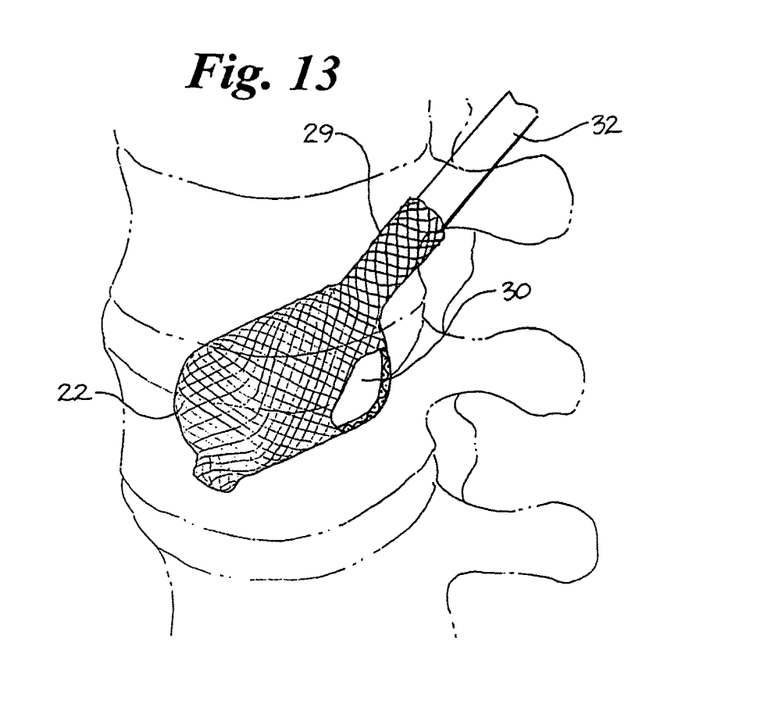
FIG. 13 is a view similar to FIG. 11 showing the approach of FIG. 12.
Figure 14:
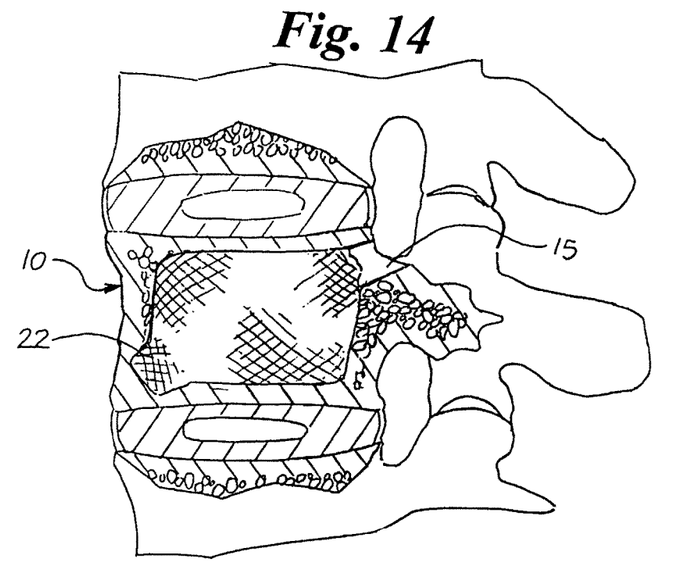
FIG. 14 shows the bag of FIG. 12 in a closed, filled and expanded position.
Figure 15:
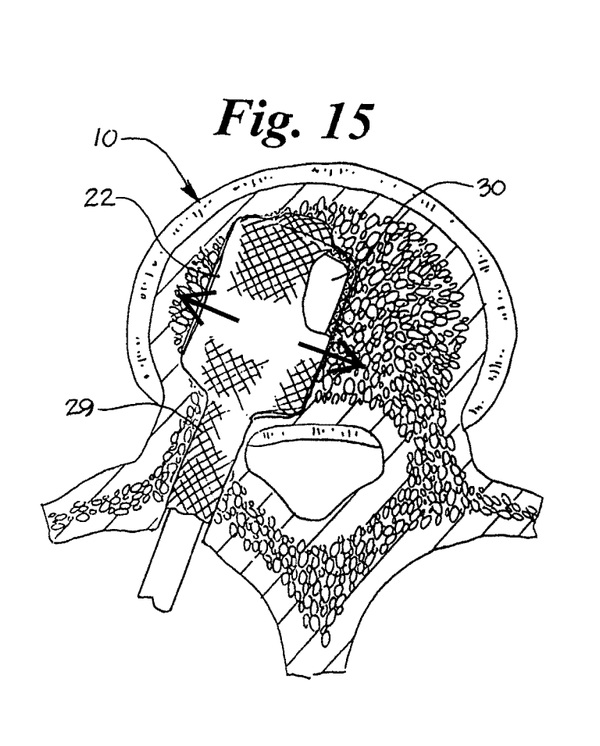
FIG. 15 is a top view of the bag system of FIG. 12 being inflated through a catheter tube.

As may best be seen in FIGS. 11, 13 and 15, the bag 22 may include a neck 29 which extends outwardly from the bag 22 to completely overlap the shape of balloon 30. The bag 22 and/or balloon 30 may each have a variety of shapes and sizes.

If desired, the expandable fabric bag 22 may be used as the sole inflation device, eliminating the Scribner et al. balloon 30 if the fabric porosity is tight and the inflation media is reasonably viscous.

Figure 16:
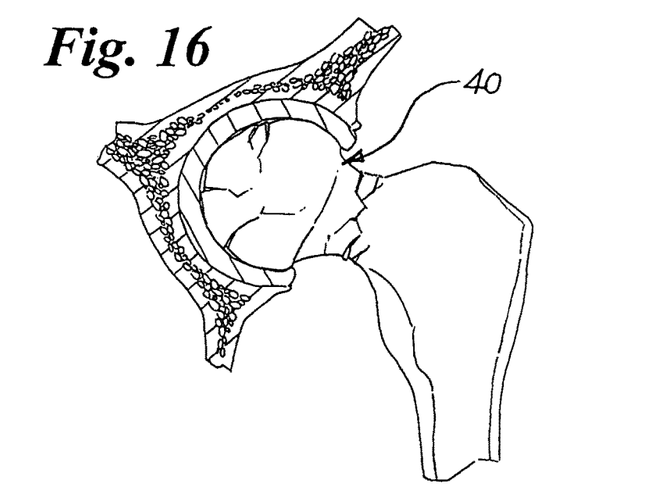
FIG. 16 shows a femoral head with avascular necrosis.
Figure 17:
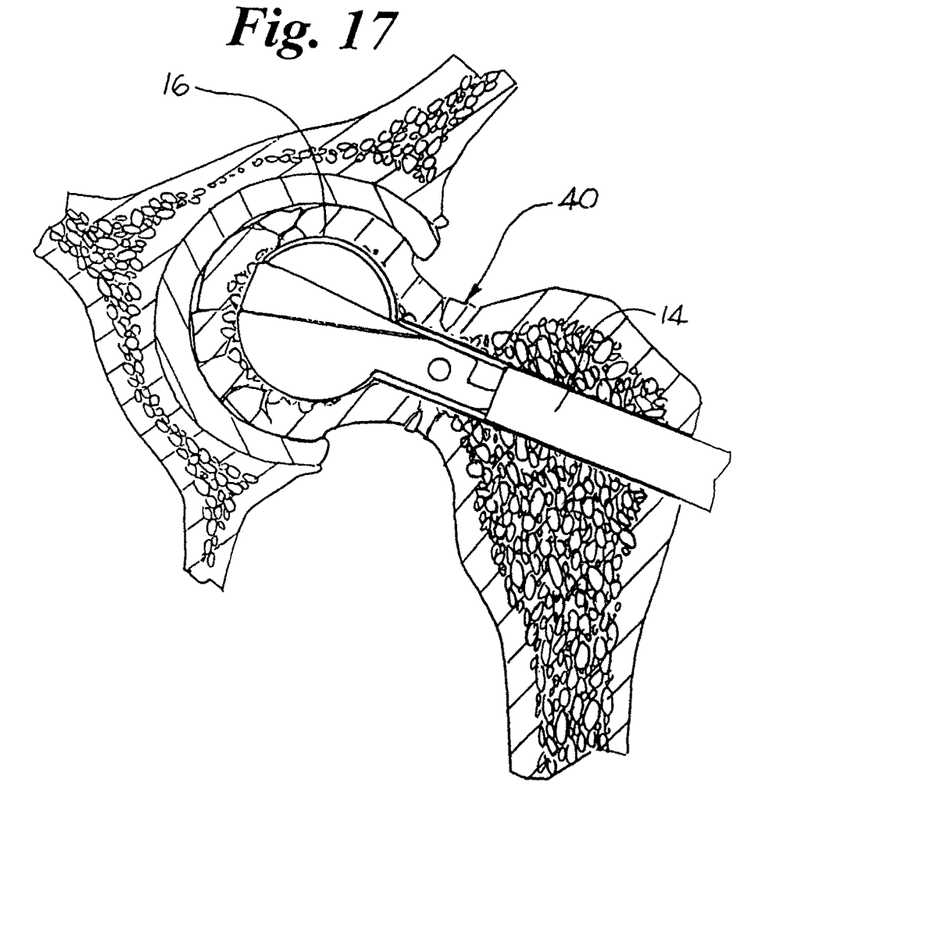
FIG. 17 shows the femoral head of FIG. 16 being reamed out.
Figure 18:
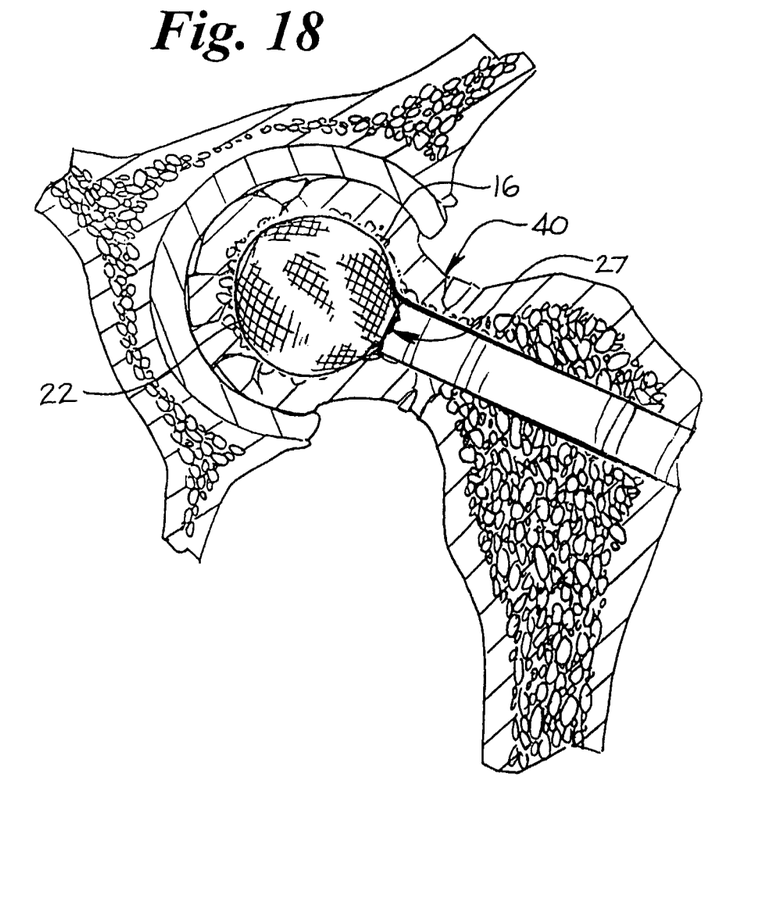
FIG. 18 shows placement of a bag system of the invention within the cavity in the femoral head.

While many of the previous embodiments have described the use of the bag 22 for repair of tissue such as a spinal body, in FIGS. 16-18 show how the bag 22 may be used in treating avascular necrosis of the femoral head. In FIG. 16, a femoral head 40 is shown which is in need of repair. FIG. 17 shows the femoral head being reamed out with a reamer 14, such as previously described. The reamer 14 forms a cavity 16. In FIG. 18, a bag 22 is shown within the cavity 16 formed within the femoral head 40. The opening 27 of the bag 22 is closed off after being filled and expanded with bone substitute material.

In an alternative embodiment, the Scribner et al. balloon, as previously described, may also be used with the bag 22 for repair of the femoral head 40.

Figure 19:
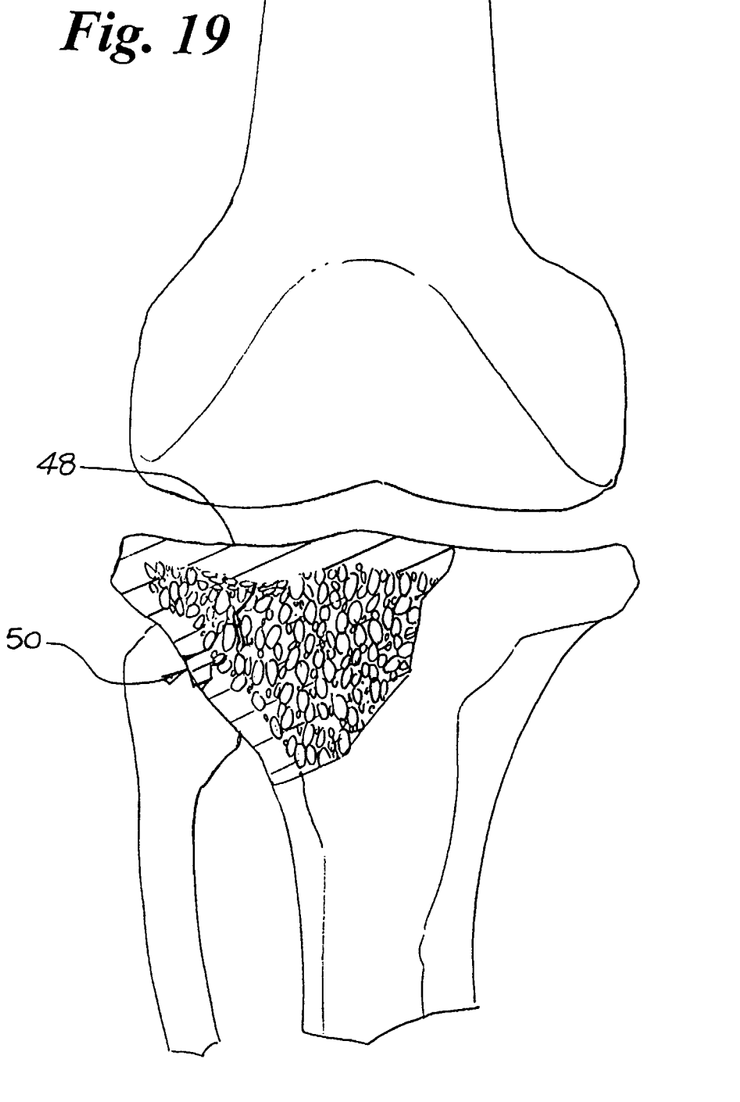
FIG. 19 is a side elevational view of a tibial plateau fracture.
Figure 20:
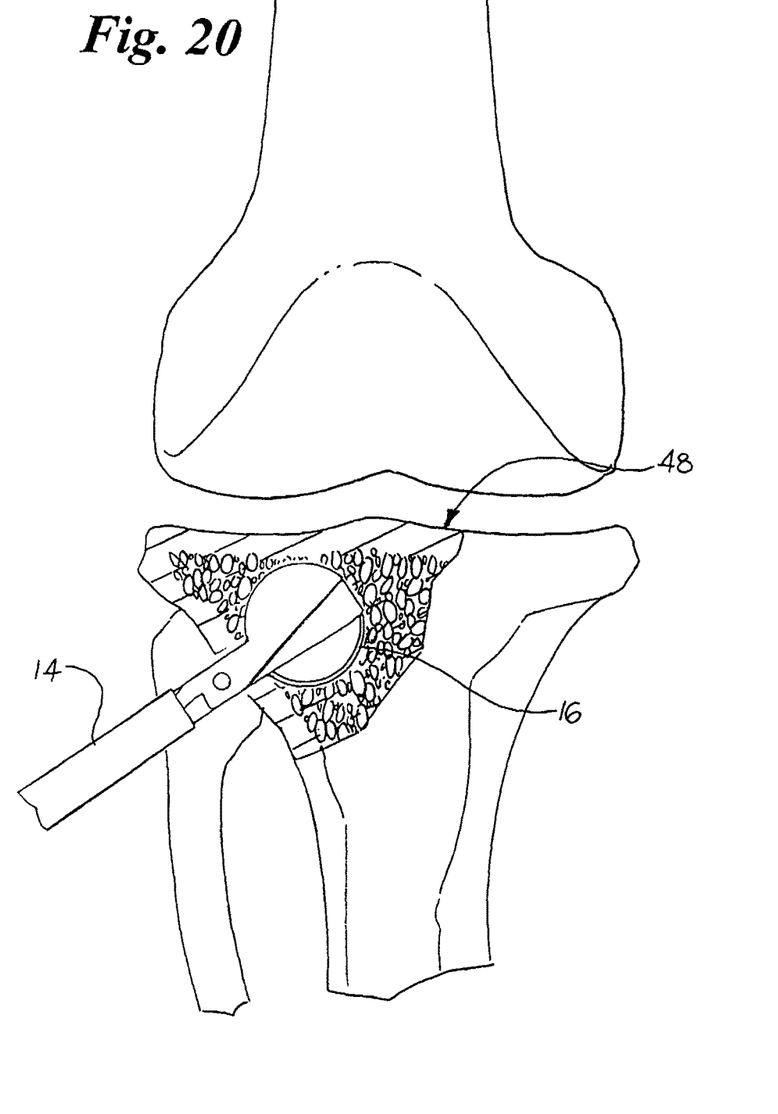
FIG. 20 is a side view of the fracture of FIG. 19 with a cavity being formed with a reamer.
Figure 21:
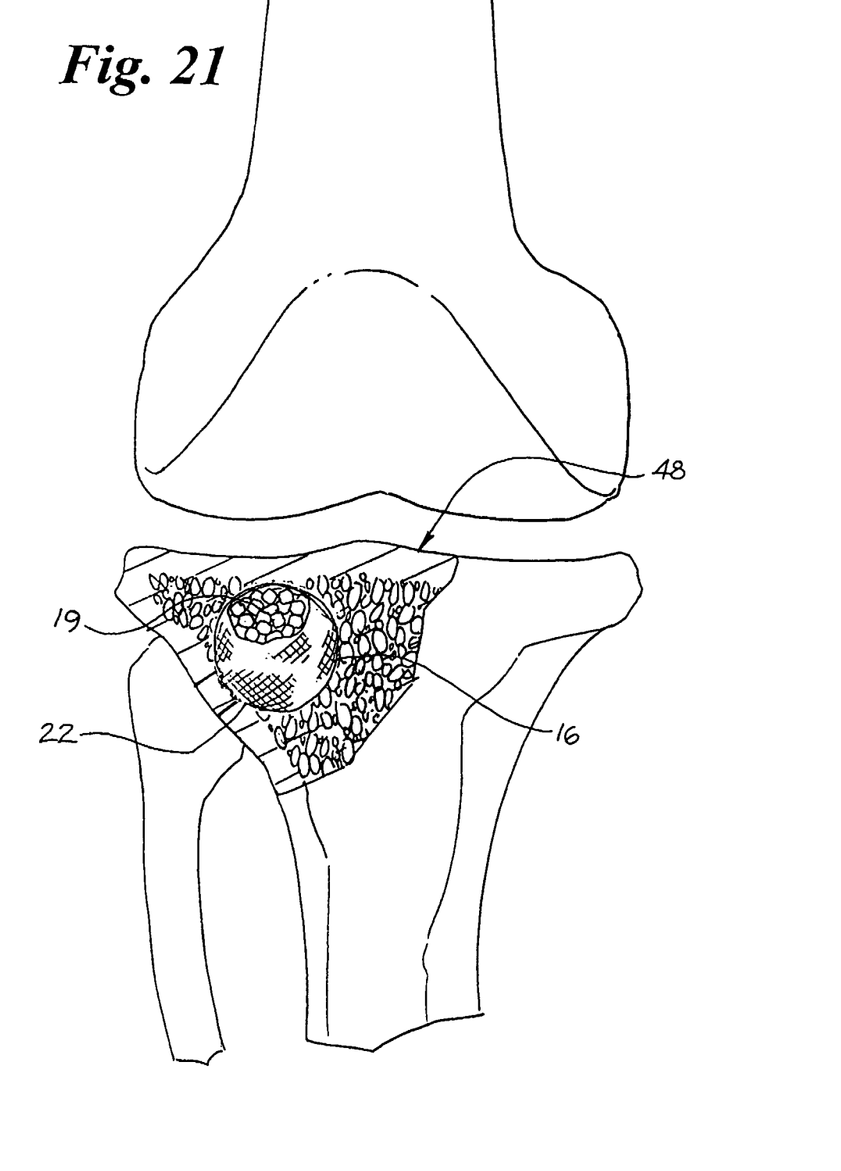
FIG. 21 shows the tibial plateau fracture repaired with an expanded inflatable fabric bag in place.

Turning to an embodiment of the invention shown in FIGS. 19-21, a tibial plateau 48 is shown having a fracture 50. The fracture 50 is repaired by forming a cavity 16 with a reamer 14, such as is shown in FIG. 20. As is shown in FIG. 21, once cavity 16 is properly reamed, bag 22 may be inserted therein and filled with bone repair media 19.

Other tissue and bone abnormalities may also be treated with the inventive methods and bag 22 described herein. The present invention is not limited to only treatment of spinal bodies, femoral heads, and tibial plateaus. The bag 22 and the methods of treatment described herein, may be utilized throughout a mammalian body to treat many types of bone and tissue abnormalities including those described herein as well as others.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g., claim 3 may be taken as alternatively dependent from claim 2; claim 5 may be taken as alternatively dependent on claim 3, claim 6 may be taken as alternatively dependent from claim 3; claim 7 may be taken as alternatively dependent from claim 3, 5 or 6; etc.).

What is claimed is:

1. A method of treating a bone abnormality in a body comprising:
    creating an access aperture to the bone abnormality;
    inserting a cavity creation tool into the access aperture of the bone abnormality to excise out a quantity of tissue to create a cavity;
    inserting a container into the cavity created by the cavity creation tool; and
    filling the container located in the cavity with fill material such that at least a portion of the fill material exits the container and enters the bone abnormality.

2. The method of claim 1, wherein the container is porous.

3. The method of claim 1, wherein the cavity creation tool is a reaming tool.

4. The method of claim 1, wherein the access aperture defines a lateral width dimension and the cavity defines a lateral width dimension, the cavity lateral width dimension being greater than the access aperture lateral width dimension.

5. The method of claim 1, wherein the access aperture defines a distally extending depth dimension and the cavity defines a distally extending depth dimension, the cavity depth dimension being greater than the access aperture depth dimension.

6. The method of claim 1, wherein the cavity is created without compaction of cancellous bone located in the vertebral body.

7. The method of claim 1, wherein the cavity is created without the use of an inflatable device disposed within the vertebral body.

8. A method of treating a fractured vertebral body comprising:
    creating at least one access opening into the vertebra;
    inserting a cavity forming tool into the access opening in the vertebra;
    forming at least one cavity in the vertebra, wherein the cavity defines a larger volume than a volume of the access opening;
    inserting an expandable container into the at least one cavity formed by the cavity forming tool through the opening, the container including a first plurality of pores of a first size and a second plurality of pores of a second size, the first size being smaller than the second size, the container defining an interior and having an exterior; and
    filling the container with fill material until the combination of fill material and container form a self-retaining rigid shape wherein the exterior of the container is substantially in contact with the vertebral bone and at least a portion of the fill material exits the container and enters the vertebral bone.

9. The method of claim 8, wherein the cavity is formed by at least one of reaming and compacting cancellous bone of the vertebra.

10. The method of claim 8, wherein the cavity forming tool is a reaming tool.

11. The method of claim 8, wherein the access opening defines a lateral width dimension and the cavity defines a lateral width dimension, the cavity lateral width dimension being greater than the access opening lateral width dimension.

12. The method of claim 8, wherein the access opening defines a distally extending depth dimension and the cavity defines a distally extending depth dimension, the cavity depth dimension being greater than the access opening depth dimension.

13. The method of claim 8, wherein the cavity is created without the use of an inflatable device disposed within the vertebral body.

14. The method of claim 8, wherein filling the container with fill material generates a mechanical force applied against the vertebral bone with which the container is in contact.

* * * * *